(12) United States Patent
Croushorn et al.

(10) Patent No.: US 9,149,280 B2
(45) Date of Patent: *Oct. 6, 2015

(54) PORTABLE PNEUMATIC ABDOMINAL AORTIC TOURNIQUET WITH SUPPLEMENTAL TENSIONING MEANS

(71) Applicant: Compression Works, LLC, Montgomery, AL (US)

(72) Inventors: John M Croushorn, Birmingham, AL (US); Richard Schwartz, Evans, GA (US); Ted Westmoreland, Greenville, SC (US)

(73) Assignee: Compression Works, LLC, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/485,704

(22) Filed: Sep. 13, 2014

(65) Prior Publication Data
US 2015/0032149 A1    Jan. 29, 2015

Related U.S. Application Data

(63) Continuation-in-part of application No. 12/150,728, filed on Apr. 30, 2008, now Pat. No. 8,834,517, which is a continuation-in-part of application No. 13/983,500, filed as application No.
(Continued)

(51) Int. Cl.
*A61B 17/00* (2006.01)
*A61B 17/132* (2006.01)
*A61B 17/135* (2006.01)

(52) U.S. Cl.
CPC ........... *A61B 17/1325* (2013.01); *A61B 17/135* (2013.01)

(58) Field of Classification Search
CPC ............ A61B 17/1325; A61B 17/135; A61B 17/132; A61B 17/1322; A61B 17/1327; A61B 17/1355; A61B 2017/12004; A61H 9/0092; A61H 2011/005; A61H 9/0078; A61H 2201/0103; A61H 2205/083; A61F 5/34; A61F 5/012; A41D 2400/14
USPC .................................................. 606/201–204
See application file for complete search history.

(56) References Cited

U.S. PATENT DOCUMENTS

| 1,679,978 A | * | 8/1928 | Konwiser et al. | ............. 606/202 |
| 2,660,174 A | * | 11/1953 | Saemann | ....................... 606/202 |
| 4,635,635 A | * | 1/1987 | Robinette-Lehman | ....... 606/202 |

(Continued)

*Primary Examiner* — Katrina Stransky
(74) *Attorney, Agent, or Firm* — The Gache Law Firm, P.C.; Russell C. Gache

(57) ABSTRACT

A portable pneumatic abdominal aortic tourniquet for occlusion of the abdominal descending aorta to restrict blood supply to a non-compressible arterial hemorrhage in or below the inguinal region is presented. The tourniquet includes an adjustable waist strap for securing it around the abdomen of a patient and a windlass rod connected to the waist strap to selectively tighten the strap as needed to tightly secure it to patient. A directed air bladder is mounted to the waist strap having a generally "V" shaped construction and is expanded for exerting directed pressure against the abdomen. Upon inflation of the air bladder and adjustment of the windlass, occlusion or restriction of blood flow through the abdominal descending aorta will occur which will achieve cessation of hemorrhage in or below the inguinal area or achieve other therapeutic effects like elevated blood pressure to enhance CPR or blood flow control to the lower extremities.

25 Claims, 10 Drawing Sheets

Related U.S. Application Data

PCT/US2012/023886 on Feb. 3, 2012.

(60) Provisional application No. 61/439,628, filed on Feb. 4, 2011, provisional application No. 60/915,642, filed on May 2, 2007.

(56) References Cited

U.S. PATENT DOCUMENTS

| | | | | |
|---|---|---|---|---|
| 4,979,953 | A * | 12/1990 | Spence | 606/202 |
| 5,193,549 | A * | 3/1993 | Bellin et al. | 600/499 |
| 5,234,459 | A * | 8/1993 | Lee | 606/203 |
| 5,295,996 | A * | 3/1994 | Blair | 606/203 |
| 5,396,906 | A * | 3/1995 | Harrold | 128/876 |
| 5,413,582 | A * | 5/1995 | Eaton | 606/202 |
| 5,423,852 | A * | 6/1995 | Daneshvar | 606/201 |
| 5,486,194 | A * | 1/1996 | Kawasaki et al. | 606/203 |
| 5,514,155 | A * | 5/1996 | Daneshvar | 606/201 |
| 5,628,721 | A * | 5/1997 | Arnold et al. | 602/19 |
| 5,643,315 | A * | 7/1997 | Daneshvar | 606/201 |
| 5,667,524 | A * | 9/1997 | Bourgeois et al. | 606/202 |
| 5,695,520 | A * | 12/1997 | Bruckner et al. | 606/204 |
| 5,792,173 | A * | 8/1998 | Breen et al. | 606/201 |
| 5,871,499 | A * | 2/1999 | Hahn et al. | 606/202 |
| 6,331,170 | B1 * | 12/2001 | Ordway | 602/19 |
| 6,746,470 | B2 * | 6/2004 | McEwen et al. | 606/202 |
| 6,884,254 | B2 * | 4/2005 | Brooks | 606/201 |
| 6,960,223 | B1 * | 11/2005 | Ambach | 606/203 |
| 7,582,102 | B2 * | 9/2009 | Heinz et al. | 606/203 |
| 8,834,517 | B2 * | 9/2014 | Croushorn et al. | 606/203 |
| 2003/0199922 | A1 * | 10/2003 | Buckman | 606/202 |
| 2004/0028540 | A1 * | 2/2004 | Peck | 417/374 |
| 2004/0098035 | A1 * | 5/2004 | Wada et al. | 606/201 |
| 2005/0113866 | A1 * | 5/2005 | Heinz et al. | 606/203 |
| 2005/0131326 | A1 * | 6/2005 | Bates et al. | 602/41 |
| 2005/0273134 | A1 * | 12/2005 | Esposito | 606/203 |
| 2006/0095072 | A1 * | 5/2006 | TenBrink et al. | 606/201 |
| 2007/0005107 | A1 * | 1/2007 | Janota | 606/203 |
| 2007/0191881 | A1 * | 8/2007 | Amisar et al. | 606/203 |
| 2010/0057120 | A1 * | 3/2010 | Kirkham | 606/203 |

* cited by examiner

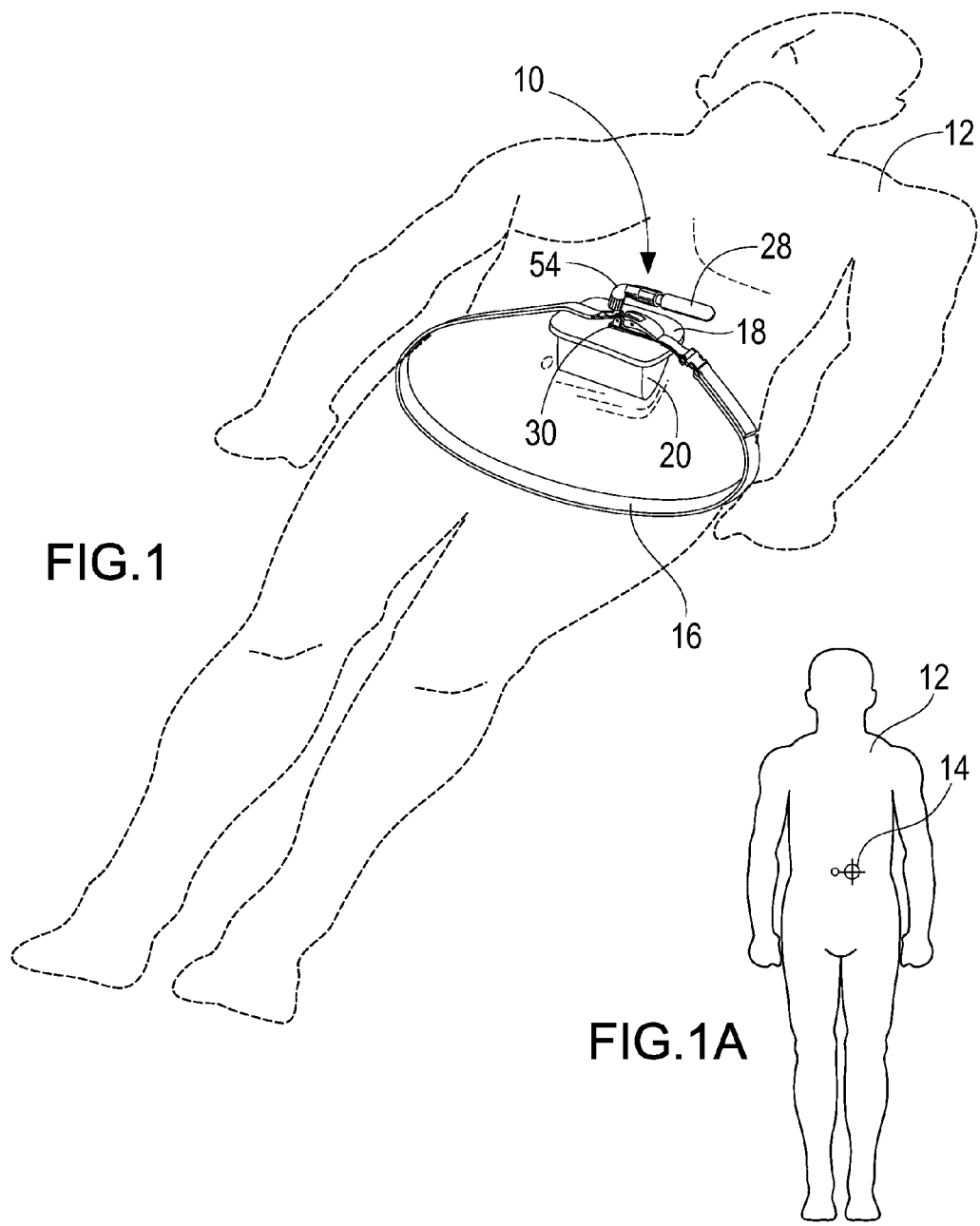

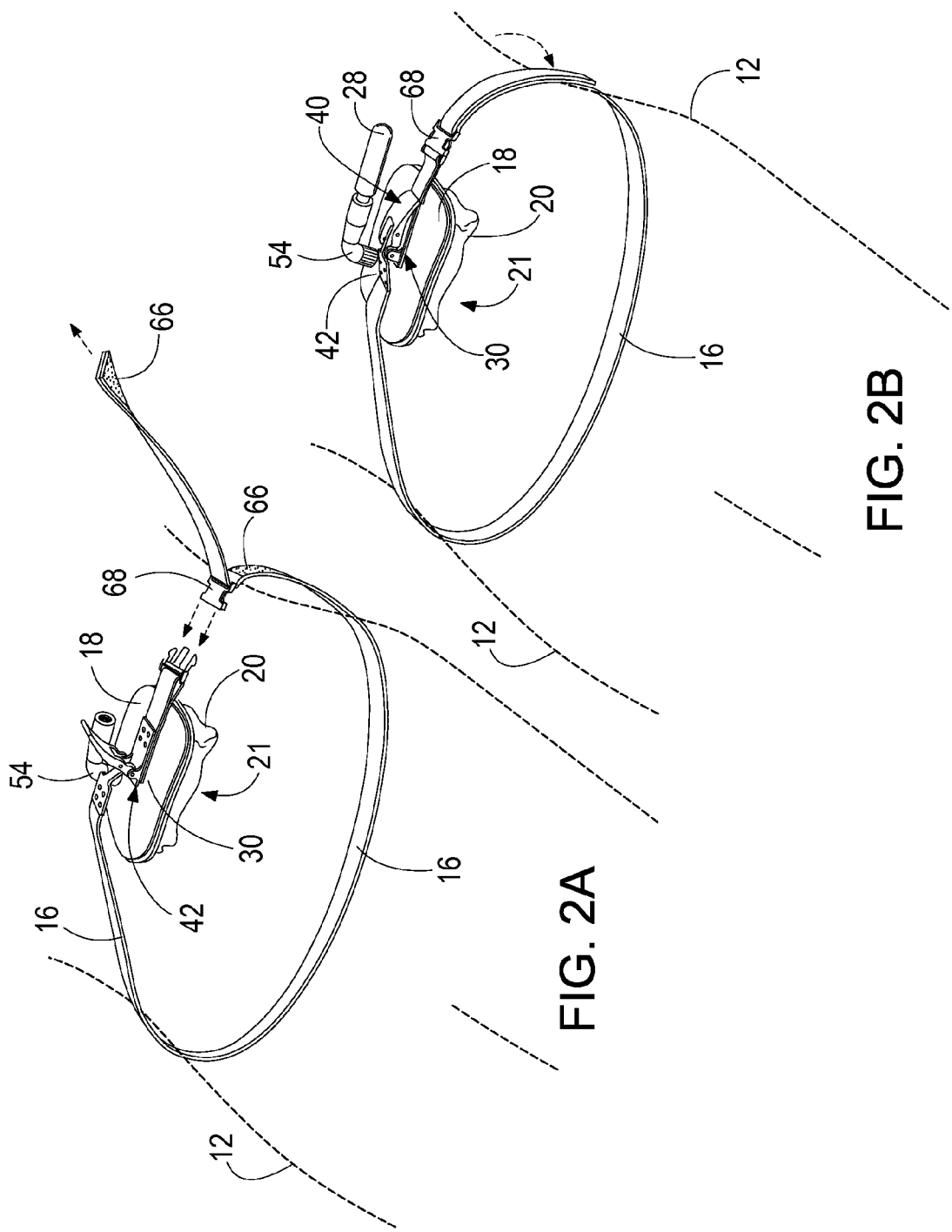

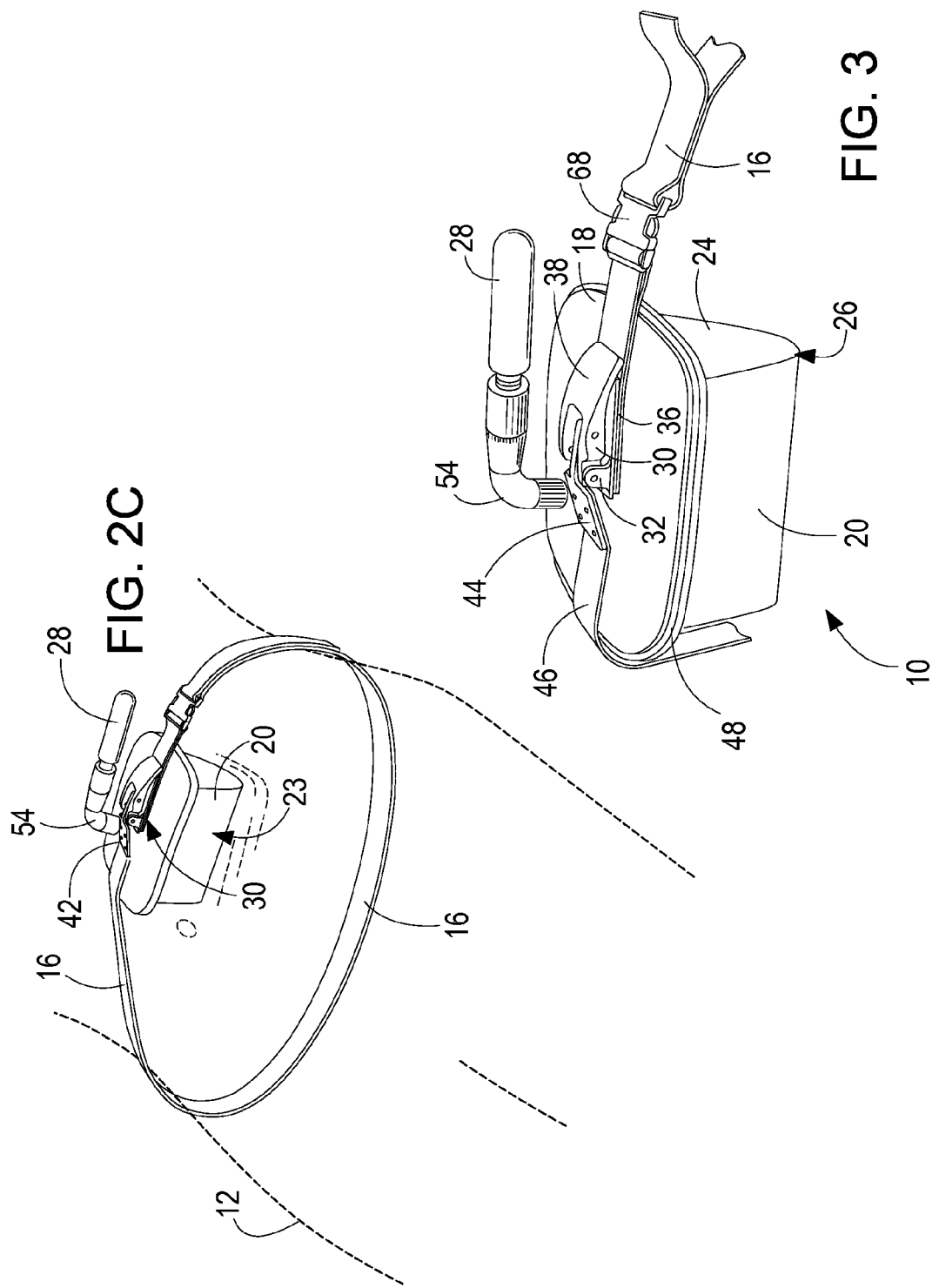

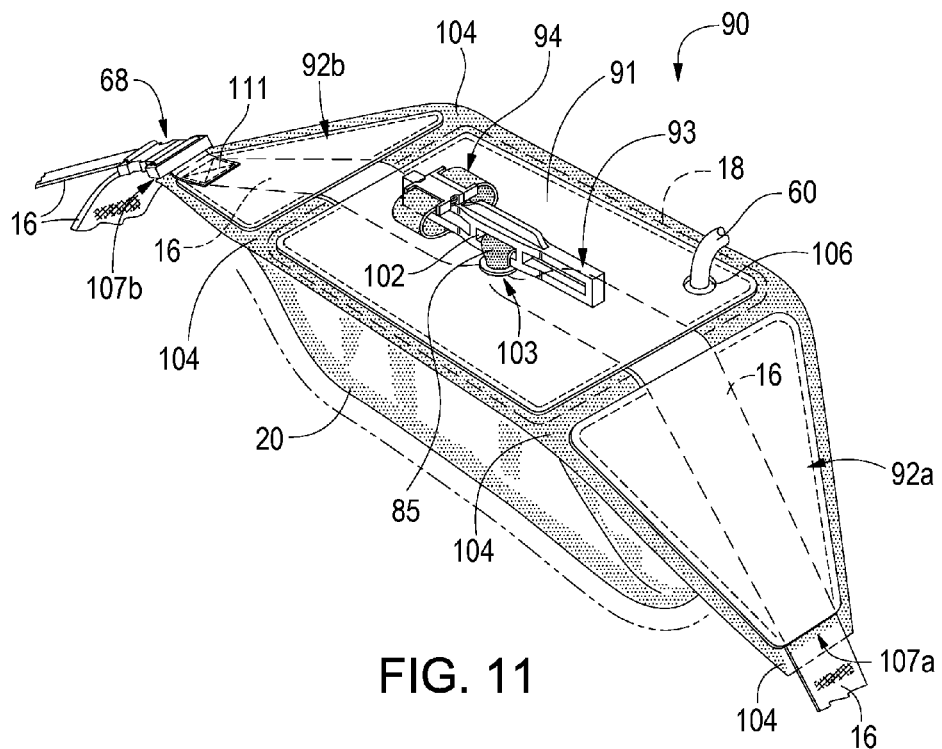
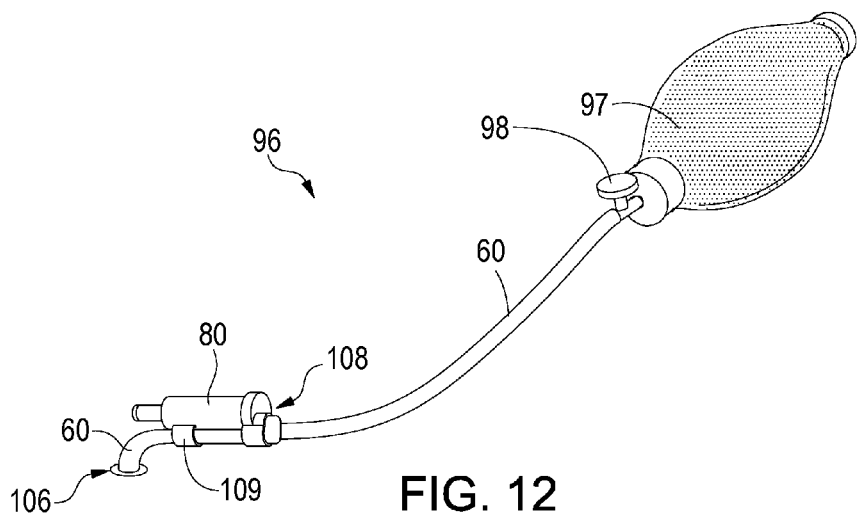

PORTABLE PNEUMATIC ABDOMINAL AORTIC TOURNIQUET WITH SUPPLEMENTAL TENSIONING MEANS

This application claims the benefit of filing priority under 35 U.S.C. §119 and 37 C.F.R. §1.78 of pending U.S. patent application Ser. No. 12/150,728 filed Apr. 30, 2008 which, in turn, claims priority to U.S. Provisional Application Ser. No. 60/915,642 filed May 2, 2007 both of which are incorporated herein by reference. This application also claims priority to pending U.S. application Ser. No. 13/983,500 received Aug. 2, 2013 in the USPTO which is the national stage entry of PCT Application Serial No. PCT/US2012/023886 which, in turn, claims priority to U.S. Provisional Application Ser. No. 61/439,628 filed Feb. 4, 2011 which is also incorporated herein by reference. All information disclosed in those prior pending applications is incorporated herein by reference.

FIELD OF THE INVENTION

The present invention relates generally to tourniquets. In greater particularity, the present invention relates to field dressings that utilize mechanical pressure to achieve homeostasis at the site of an injury. In even greater particularity, the present invention relates to strap-on tourniquets positioned to apply pressure on the body to stop bleeding.

BACKGROUND OF THE INVENTION

Various tourniquet devices that use a wide variety of clamping and/or pneumatic means to apply pressure to various limbs on the body have been attempted. However, prior attempts at cessation of hemorrhage from the major blood vessels of the body at or below the inguinal area have not been no completely successful, especially if attempted on gross battle-field wounds such as leg amputations due to anti-personnel mines or high velocity bullet percussion wounds to the lower extremities. Quite often, such wounds do not provide a satisfactory compressible site to stop arterial hemorrhages and require occlusion of the abdominal descending aorta to cut-off the blood supply to the wound in order to protect the patient's life.

However, compressing the abdominal descending aorta is a difficult exercise. One of the major obstacles to providing an effective portable abdominal aortic tourniquet is in providing a focused compression force over the targeted area on the abdomen to achieve aorta occlusion. Typically, most tourniquets apply a constricting force around the circumference of a limb or over a broad area to reduce total blood flow through the limb. Such a broad application of force is ineffective to reduce or occlude blood flow through the descending aorta proximal to the bifurcation in the abdomen due to the deep location of the aorta in the body. A strong focused pressure is required to reach the descending aorta and reduce blood flow. Prior inventions fail to show or disclose a technique for focusing a compression force in the abdomen to operate as an abdominal aortic tourniquet.

For example, US Patent Application Publication No. 2007/0191881 A1 (Amisar et al.) shows a tourniquet that includes a pressure source and a selector leaver attached to a cam to facilitate manual selection of a designated pressure. This tourniquet is designed to apply pressure around a limb. There is no teaching in the patent that this device would be effectively useable as an abdominal aortic tourniquet. Further, the air bladder is not a directed air bladder that would focus the compression force, but is rounded to wrap around the limb and spread the pressure force over a broad area. Such a broad application of constricting force is unusable if intended to reduce or occlude circulation through the descending aorta for a non-compressible arterial hemorrhage in the abdominal region.

U.S. Pat. No. 5,234,459 (Lee) shows an inflatable balloon for use in a tourniquet. The patent discloses a manual pump for inflating the balloon. There is no disclosure of the balloon having a directed shape for focusing a compression force, or that the tourniquet is in any way designed to work as an abdominal aortic tourniquet. This tourniquet is representative of a vast majority of pneumatic prior art tourniquet devices which completely fail to address the specific problems associate with providing an effective abdominal aortic tourniquet U.S. Pat. No. 6,884,254 (Brooks) shows a tourniquet system that includes a leverage assisted clamp means for tightening the strap around a limb. This patent is representative of a large section of the prior art that uses mechanical means, as opposed to pneumatic to provide a constricting force around a limb. Again, such devices fail to provide the directed compression force required to restrict blood flow through the descending aorta.

Therefore, what is needed is a portable abdominal aortic tourniquet that can be rapidly applied under field conditions that includes a means for tensioning the tourniquet upon a patient rapidly and with sufficient force to ensure abdominal aortic occlusion.

SUMMARY OF THE INVENTION

The invention is a pneumatic abdominal aortic tourniquet that has an adjustable waist strap for securing it around a patient's abdomen. A rigid base plate is carried by the waist strap having a width greater than the waist strap so that the base plate extends laterally outward from the waist strap to provide a stable base for positioning over a selected area of the patient's abdomen. An air bladder is affixed to the underside of the base plate. Initially, the air bladder is kept in a deflated condition collapsed against the base plate, but is upon actuation of the tourniquet expands to an inflated condition and extends outwardly from the bottom side of the base plate. The directed air bladder has a generally "V" cuneiform shaped construction so that a wide end of the directed air bladder is generally carried on the bottom side of the base plate and a narrow end of the directed air bladder presses against the abdomen when in the inflated condition. The narrow end of the bladder extends into the abdomen of the patient so that a constricting force is focused against a narrow defined area within the abdomen causing restriction of blood flow through the abdominal aorta. The tourniquet includes an air source operatively connected in fluid communication with the directed air bladder for operating the directed air bladder between the deflated condition and the inflated condition. The tourniquet also includes a tensioning means comparable to a mechanical "windlass" that allows a user to further tighten the base of tourniquet against the patient thereby facilitating effective aorta occlusion.

Other features and objects and advantages of the present invention will become apparent from a reading of the following description as well as a study of the appended drawings.

BRIEF DESCRIPTION OF THE DRAWINGS

A tourniquet incorporating the features of the invention is depicted in the attached drawings which form a portion of the disclosure and wherein:

FIG. 1 shows a perspective view of a pneumatic abdominal aortic tourniquet attached in an operative condition to a patient according to the present invention;

FIG. 1A shows a representative human form indicating where the pneumatic abdominal aortic tourniquet is to be applied according to the present invention;

FIG. 2A shows a perspective view of the pneumatic abdominal aortic tourniquet in a deflated condition being secured around a patient's lower abdomen according to the present invention;

FIG. 2B shows a perspective view of the waist strap for the pneumatic abdominal aortic tourniquet being tightened around a person's lower abdomen according to the present invention;

FIG. 2C shows a perspective view of the pneumatic abdominal aortic tourniquet in an inflated condition according to the present invention;

FIG. 3 shows a detailed perspective view of the pneumatic abdominal aortic tourniquet according to the present invention;

FIG. 11 shows a magnified view of a portion of the embodiment shown in FIG. 10; and, FIG. 12 shows an expanded view of the manual inflation system of the embodiment shown in FIG. 10.

DESCRIPTION OF THE PREFERRED EMBODIMENTS

Figure 4A:
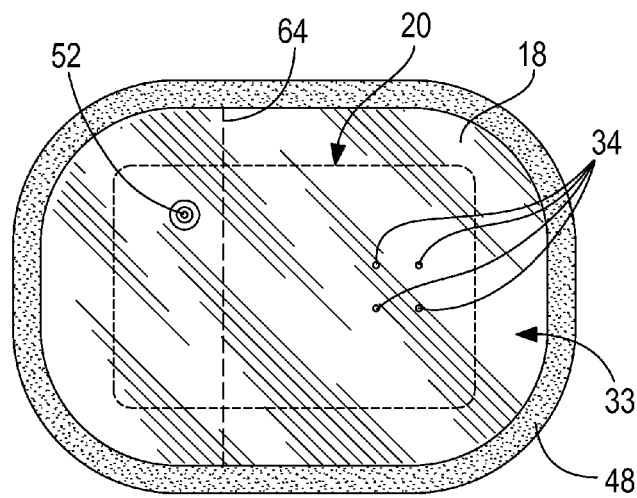
FIG. 4A shows a top plan view of the base plate of the pneumatic abdominal aortic tourniquet according to the present invention.

Referring to the drawings for a better understanding of the function and structure of the invention, and starting with FIG. 1, a pneumatic abdominal aortic tourniquet, designated generally as 10, is shown secured around the lower abdomen of a person 12 for restricting blood flow through the descending aorta proximal to its bifurcation in the lower abdomen to deal with a non-compressible arterial hemorrhage. Referring to FIG. 1A, the tourniquet is arranged over the abdomen to apply localized pressure across a pressure point 14 to restrict blood flow in downstream hemorrhage locations from the point of application.

Referring to FIGS. 1 through 3, pneumatic abdominal aortic tourniquet 10 includes an adjustable waist strap 16 for securing the tourniquet around the abdomen of a patient 12. A rigid base plate 18 is carried on waist strap 16. Base plate 18 is constructed and arranged to have a width greater than waist strap 16 so that base plate 18 extends laterally outward from waist strap 16 to provide a stable base for positioning over and across a selected area, such as a preferred pressure point 14 (FIG. 1A) of the abdomen.

A directed air bladder 20 is carried on a bottom side 22 of base plate 18. As shown in FIGS. 2A and 2B, directed air bladder 20 has a deflated condition, designated generally as 21, for initial application to a patient wherein directed air bladder 20 is generally collapsed against base plate 18. As shown in FIG. 2C, directed air bladder 20 is then operated to an inflated condition designated generally as 23, wherein the directed air bladder 20 is expanded to extend outwardly from bottom side 22 of base plate 18 to exert pressure on a localized area of the abdomen. Referring to FIG. 4C, directed air bladder 20 is constructed and arranged to have a generally "V" shaped construction so that a wide end, designated generally as 24, of directed air bladder 20 is carried on bottom side 22 of base plate 18. A narrow end 26 of directed air bladder 20 presses against the abdomen in a generally parallel orientation relative to the base plate, when in the inflated condition so that a constricting force caused by inflation of the directed air bladder 20 against the abdomen is focused against a narrow, elongated defined area to penetrate the patient's abdomen and restrict blood flow through the abdominal aorta.

Referring to FIG. 3, an air source 28 is operatively connected in fluid communication with directed air bladder 20 for operating the directed air bladder between the deflated condition 21 and inflated condition 23. In one embodiment the air source 28 comprises a compressed gas cartridge, such as a $CO_2$ cartridge, known to those skilled in the art. As seen, tourniquet 10 may include a compression latch 30 affixed to base plate 18 and operatively associated with waist strap 16 for tightening waist strap 16 around the abdomen. Preferably, compression latch 30 includes a latch base 32 mounted to a top portion 33 of base plate 18 in a fixed arrangement.

Referring now to FIG. 4A, openings 34 may be included in base plate 18 for receiving rivets, screws or the like for mounting latch base 32 to top side 33 of base plate 18 in a secure arrangement. A first distal end 36 of waist strap 16 is disposed between latch base 32 and top side 33 (see FIGS. 4B-4C) of base plate 18 to secure base plate 18 to waist strap 16. A latch arm 38 is pivotally mounted to latch base 32 and is operable between a closed position, designated generally as 40, wherein latch arm 38 is adjacent latch base 32, and an open position, designated generally as 42 (see FIG. 2A), extending upward from latch base 32. A terminal pivot arm 44 is pivotally carried by latch arm 38 having a second distal end 46 of waist strap 16 secured thereto. Terminal pivot arm 44 moves from a relaxed position (FIG. 2A) when latch arm 38 is in open position 42, to a tightened position (FIGS. 2B and 2C) when latch arm 38 is moved to closed position 40 so that waist strap 16 is shortened to tighten around the abdomen.

Figure 4B:
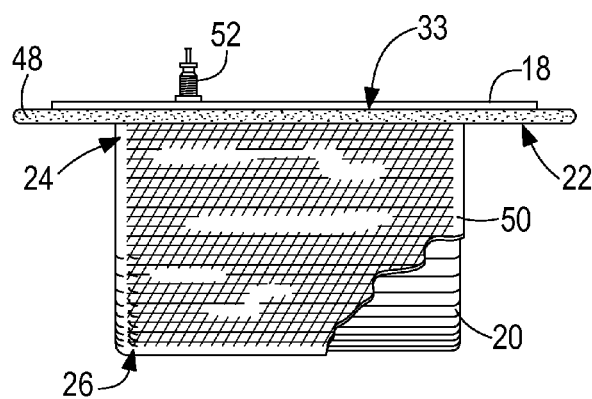
FIG. 4B shows a front elevation view and cut-away of the base plate carrying the inflatable air bladder and protective sleeve covering the air bladder according to the present invention.
Figure 4C:
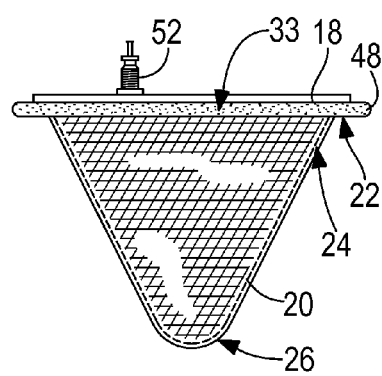
FIG. 4C shows a side elevation view of the base plate carrying the inflatable air bladder according to the present invention.

Referring to FIGS. 4A-4C, a foam pad 48 may be carried on the bottom side 22 of base plated 18 disposed between directed air bladder 20 and base plate 18 to cushion base plate 18 against the abdomen when the directed air bladder is in a deflated condition 21. Preferably, a peripheral edge of foam pad 48 extends beyond a peripheral edge of base plate 18 on all sides for cushioning against the abdomen before inflation of directed air bladder 20. A foam pad which is about 0.5 cm thick and extends beyond the edges of the base plate by 1 cm is suitable for operation.

Focusing on FIG. 4B, a protective bladder sleeve 50 may be provided surrounding directed air bladder 20 suitable for both inflated and collapsed conditions 21 and 23, to resist puncture and protect against environmental exposure of directed air bladder 20. Preferably, protective bladder sleeve 50 is attached to directed air bladder 20, such as by using an adhesive or making protective bladder sleeve 50 form fitting so that protective bladder sleeve 50 is collapsed against directed air bladder 20 when in a deflated condition 21.

Referring again to FIGS. 4A-4C, an inflation control valve 52 is carried by directed air bladder 20 and is in fluid communication with air source 28 and an interior cavity of directed air bladder 20. Valve 52 controls the flow of air into and out of directed air bladder 20 for operation between inflated condition 23 and deflated condition 21. Preferably, inflation control valve 52 is a Presta valve or a Schrader valve. Valve 52 extends through base plate 18 for cooperating with air source 28 on top side 33 of base plate 18. A pressure gauge may also be operatively associated with directed air bladder 20 for warning if the pressure is dropping in the bladder or if a maximum pressure has been reached. A guide marker 64 may further be carried on base plate 18 for helping align base plate 18 on the abdomen over and across the abdominal aorta as indicated by pressure point 14 of FIG. 1A.

Figure 5A:
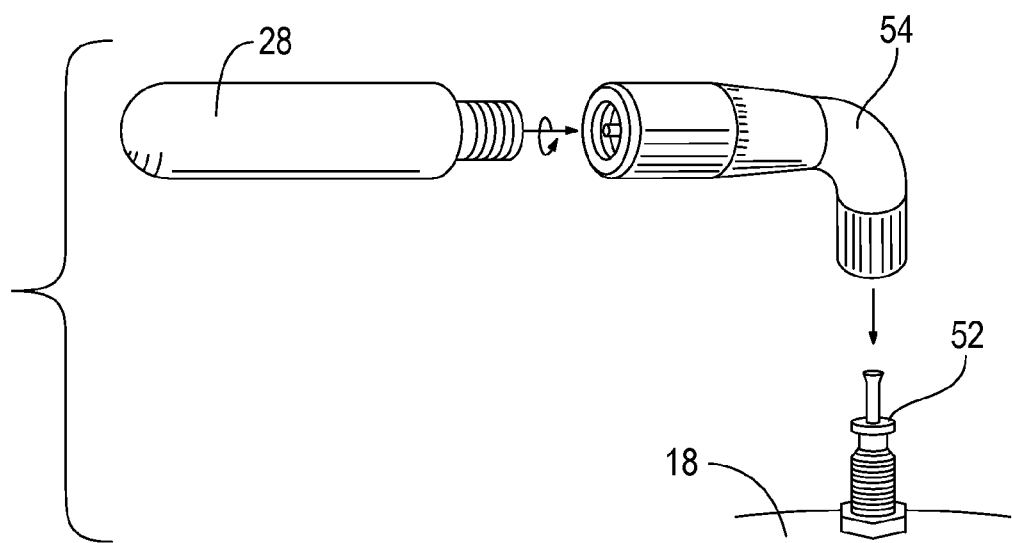
FIG. 5A shows a detailed exploded view of the air source, elbow connector and inflation control valve according to the present invention.

Referring to FIG. 5A, an elbow connecting valve 54 is preferably disposed between inflation control valve 52 and air source 28, in the form of a compressed gas cartridge, extends generally parallel to base plate 18 when engaged with elbow connecting valve 54. This provides a lower profile to the design to help avoid accidental contact with air source 28 that may result in disengagement and deflation of directed air bladder 20.

Figure 5B:
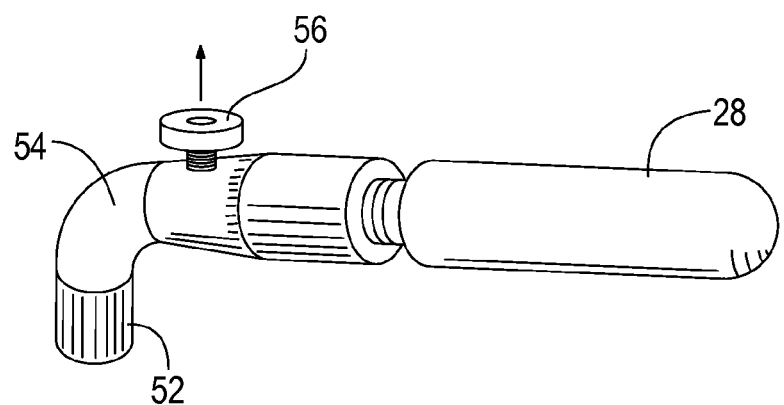
FIG. 5B shows an alternative embodiment of the elbow connector according to the present invention.

Referring now to FIG. 5B, in a further embodiment, a pressure relief valve 56 is carried by elbow connecting valve/conduit 54 which is operatively associated with directed air bladder 20 through inflation control valve 52 for adjusting an air pressure within directed air bladder 20 when in inflated condition 23. Pressure relief valve 56 may alternatively be carried at an alternative location such as directly on air bladder 20, and is not limited to being disposed on elbow connecting valve 54, which is illustrated as the preferred location in the present embodiment.

Figure 6:
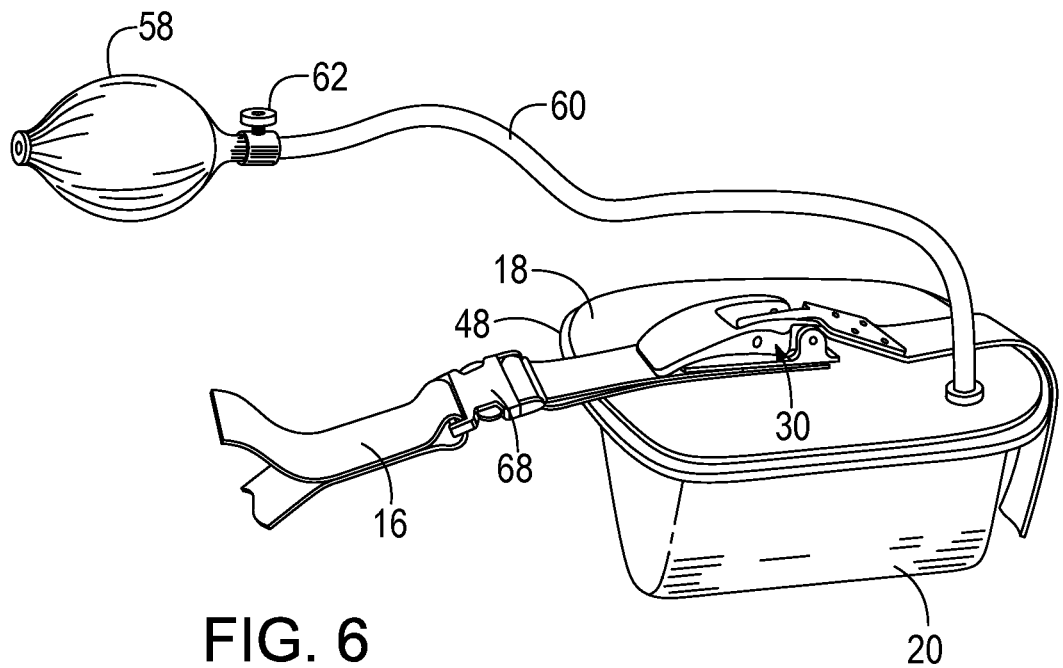
FIG. 6 shows an alternative embodiment of the pneumatic abdominal aortic tourniquet having a bulb type inflation pump according to the present invention.

Referring to FIG. 6, in a further embodiment, air source 28 is replaced by a manual bulb pump 58 and an air supply line 60 extending from bulb pump 58 to directed air bladder 20 through base plate 18 for injecting air into directed air bladder 20 when bulb pump 58 is operated. Preferably, a pressure relief valve 62 is carried by air supply line 60 for adjusting the air pressure within directed air bladder 20 when in inflated condition 23.

Preferably, waist strap 16 is constructed of 4 cm wide, 120 cm long, nylon webbing. Cooperating hook and loop fasteners 66 (FIG. 2A) may also be provided for securing loose ends of strap 16 onto itself once the strap is drawn tight around the patient's abdomen. Waist strap 16 is of sufficient length to go around the torso just above the iliac crest and includes enough slack or extra length to facilitate tightening. A quick connect buckle 68 is provided on waist strap 16 for quickly attaching and detaching waist strap 16 around the torso.

Base plate 18 is preferably made of injected molded ridged plastic material. Base plate 18 serves two primary purposes: first, it connects the pressure application mechanism—the directed air bladder 20—to waist strap 16; and second, base plate 18 provides a stable platform for anchoring air bladder 20 on the abdomen to prevent pivotal movement when in an inflated condition 23.

As may be more easily seen in FIGS. 2A-2C, in use waist strap 16 is fed around the patient's body 12 with waist strap 16 lying above the iliac crests. Buckle 68 is then connected to secure waist strap 16 around the torso and base plate 18 positioned just left of midline aligned with marker 64 such that the apex of the bladder extends across pressure point 14 (FIG. 1A). The slack is then removed from waist strap 16 and the extra strap 16 is secured onto itself using hook and loop connectors 66. Compression latch 30 is operated from open position 42 to closed position 40 to further tighten waist strap 16. Air source 28 is applied to elbow 54, typically by screwing a threaded end of a $CO_2$ cartridge into a complementary threaded receiver on elbow connector valve 54. The cartridge 28 is screwed to its maximum depth to penetrate the cartridge. The cartridge is gently unscrewed slightly to release the compressed gas into directed air bladder 20 through inflation control valve 52. Pressure relief valve 56 may be operated to fine tune the application of force by directed air bladder 20 and the flow of $CO_2$ can be stopped by screwing the cartridge into elbow connector valve 54. A pressure indicator may be incorporated on the device to warn if high pressure exists in the bladder or if pressure falls unacceptably. Generally the bladder is inflated until the desired effect of cessation of bleeding occurs, or the desired effect of preload return to the heart is achieved. A manual bulb pump may also be utilized and would be operated in the same way as with a blood pressure cuff system.

Figure 7:
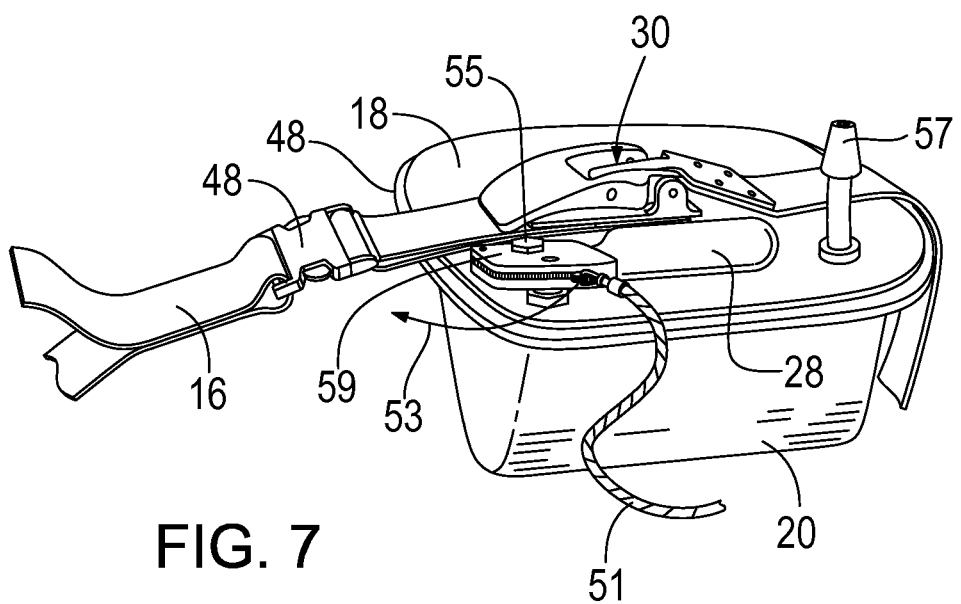
FIG. 7 shows an alternative embodiment of the pneumatic abdominal aortic tourniquet according to the present invention.

Another embodiment of the invention is illustrated in FIG. 7. Strap 16, base plate 18, air bladder 20, air source 28, compression latch 30, foam pad 48 and quick connect buckle 68, are as described above. A compartment 59 (not shown) protects the connection between the air source 28 and the bladder 20. A closure 53 such as a zipper closes the compartment and a lanyard 51 provides assistance in rapidly accessing the connection. An adaptor 57 provides for an alternative access to the air bladder 20 such as for connecting an auxiliary air pump, an auxiliary pressure relief valve, or for manually blowing up the bladder in the case of air source inoperability.

The tourniquet of the present invention is intended for use in field trauma situations in and under extreme conditions. In such environments, timing is of the utmost importance and mere seconds can determine whether a wounded individual survives. As a result, rapid deployment of the tourniquet is critical. Further, embodiments of the invention will be described with reference to FIGS. 8, 9, 10, 11, and 12 that provide features for rapidly securing the tourniquet and expanding the bladder to a desired pressure.

Figure 8:
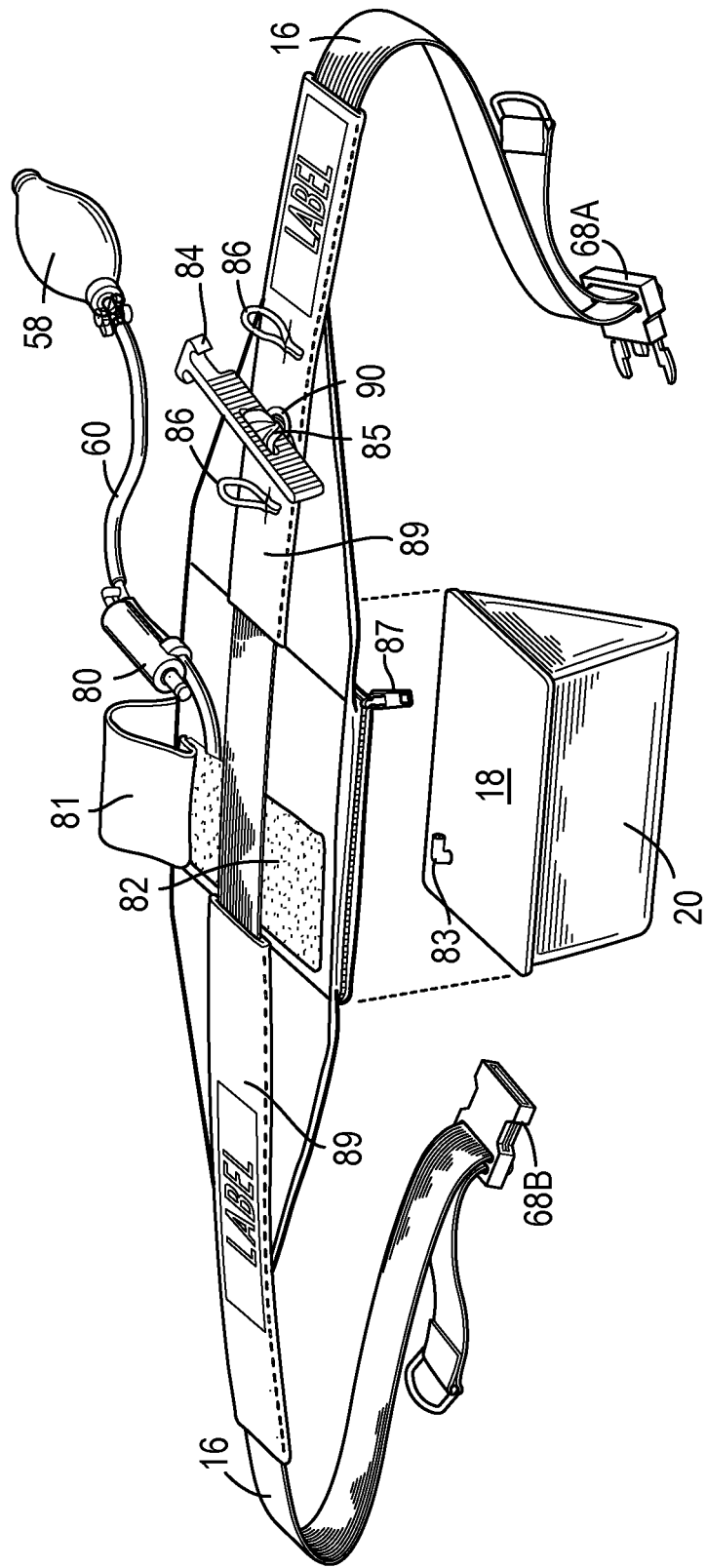
FIG. 8 shows an alternative embodiment of the pneumatic abdominal aortic tourniquet according to the present invention in partial exploded view.
Figure 9:
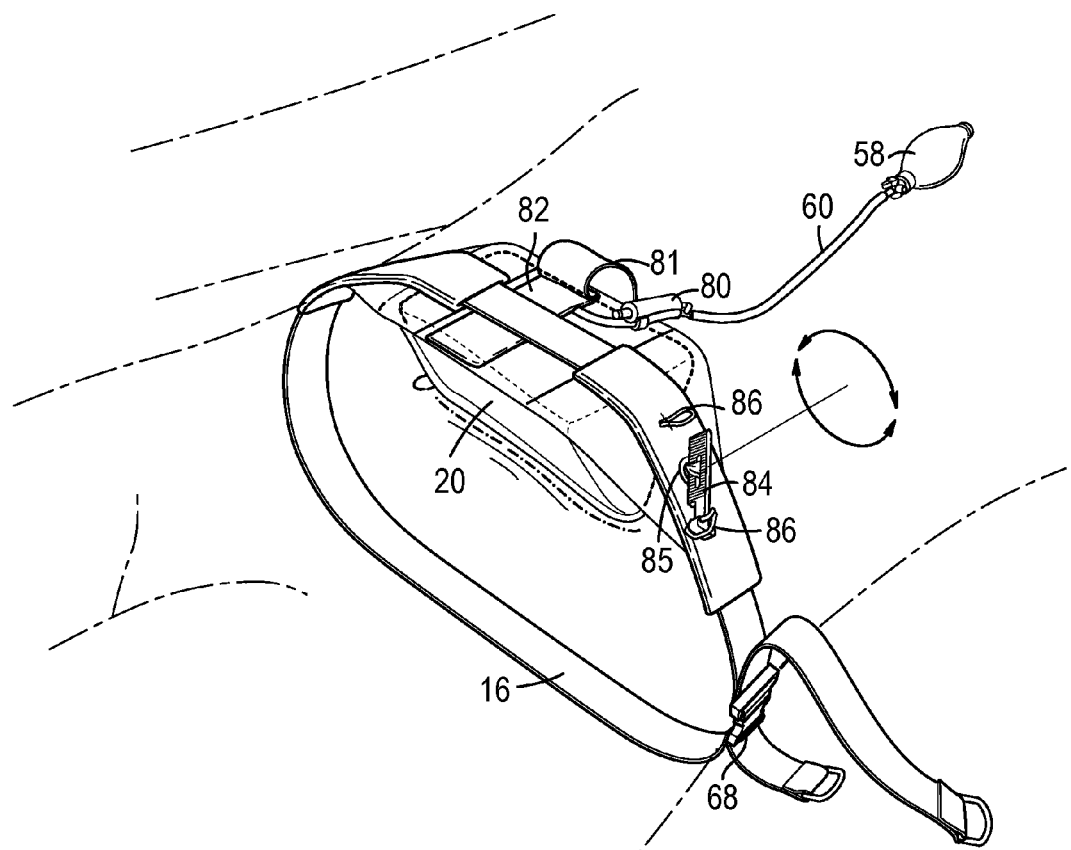
FIG. 9 shows an alternative embodiment of the pneumatic abdominal aortic tourniquet according to the present invention as in use.

In FIG. 8 a further embodiment is illustrated in partially exploded view and in use in FIG. 9. A storage device, consisting of a pad 82 and cover 81, provides a storage area for the manual bulb pump 58, the air supply line 60 and a pressure relief valve 80 which can all be gathered in serpentine fashion, laid on the pad and covered with the cover which preferable forms a closure. The closure can be secured by a hook and loop system such as Velcro®. In one embodiment the tourniquet is intended for one time use and the cover can be irreversibly removed from the pad for access to the contents of the storage area formed by the pad and cover. A connector 83 connects the air bladder to the manual bulb pump and allows the bladder to be replaced in the case of failure. A windlass rod 84 is connected to a portion of the strap 85 to allow for rapid tightening of the device. Once the tourniquet is applied and the bladder expanded it is difficult to tighten the strap through normal means like pulling a free end of strap 16 beyond buckle 68. It is also not desirable to remove or loosen the tourniquet once it is in place. However, the windlass rod 84 can easily be rotated thereby drawing the strap tighter around the patient to place more pressure on the abdomen. When the appropriate pressure is achieved the windlass rod can be inserted into a retention means 86, such as for example a simple loop, thereby securing the windlass rod in place (see FIG. 9). The windlass rod 84 includes a center slot or eyelet through which strap 16 may be routed. A seamless portion of strap 85 travels through grommet 90 in the center of the front shroud 89 of the device and then through the windlass rod and back through the grommet 90 again. The windlass rod may then be turned either clockwise or counter clockwise until the device is firmly tightened around the waist of the patient and secured with the retention means 86 affixed to the top of the device. As shown, rod 84 may have an enhanced surface texture to facilitate griping while turning, and it may have an enlarged end portion around which the retention means may pass to ensure the rod 84 does not disengage from its tightly wound state. The retention means may also be segmented with a segment sewn onto one end of the top portion of the shroud and the other end secured around a portion of the windlass rod by either a snap or buckle.

An alternative embodiment of the tourniquet device may include a three piece shroud to aid in routing of the waist strap through its top. Such a configuration also allows for labeling and enhanced functionality of the windlass rod. For example, the shroud may be made from 1.2 mil thick reinforced plastic weave sheeting that is water gel cut to form. The three pieces may be made up of a center shroud covering the top/front of the tourniquet with two side pieces serving as covers or "wings" on the device. The top-center shroud portion provides for labeling and for holding a windlass grommet, windlass retention strap, and an elbow connector from the bladder to the inflation system. The shroud would be typically sewn onto the device, with portions of the perimeter of the shroud sewn to form a channel through which the waist strap 16 may travel.

Figure 10:
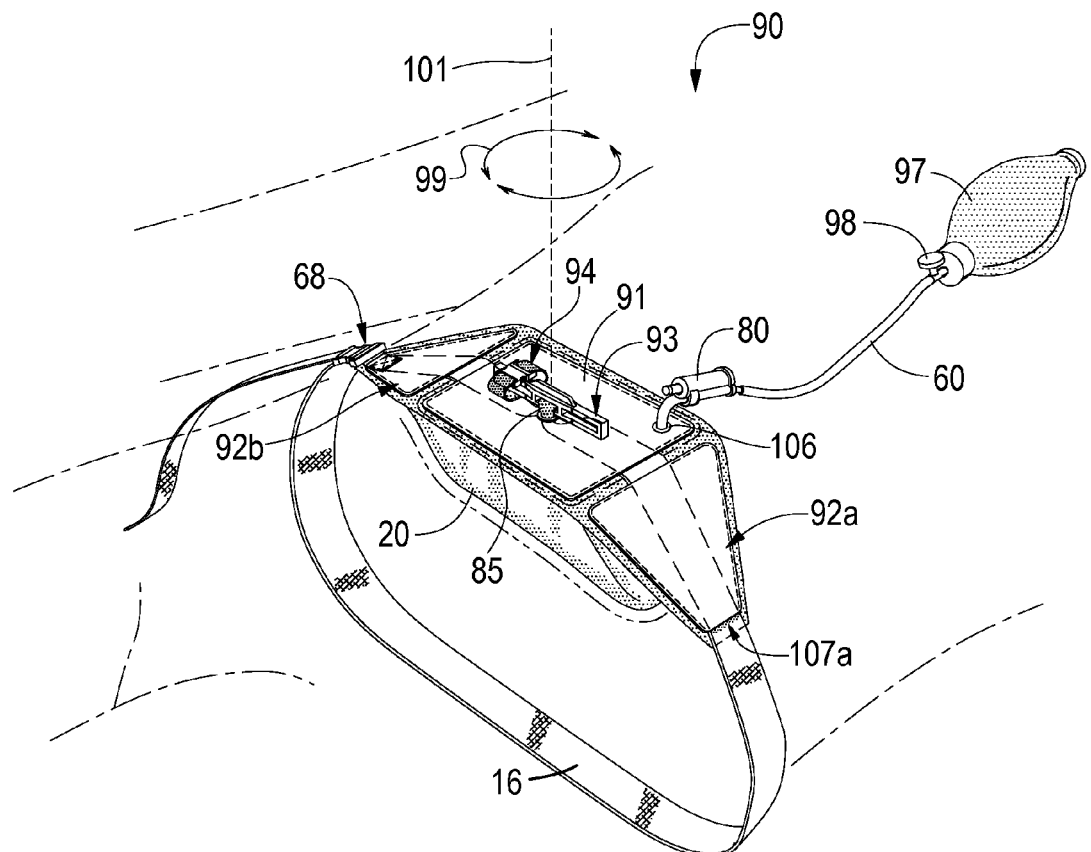
FIG. 10 shows an alternative embodiment of the pneumatic abdominal aortic tourniquet according to the present invention as in use.

An example of such a described embodiment may be seen in FIGS. 10-12. Shroud 104 is an integral piece of material typically made from resilient, woven nylon material, such as Cordura®, which is gel cut to form and has seams RF welded together to shape the shroud. The shroud extends over the top of base 18 and depends downward on each side to form triangular wings or sections. The top center panel of the shroud 104 supports a top panel 91 and the shroud side sections support delta shaped panels 92a,b made of resilient plastic. The top and side panels are stitched onto the shroud and provide additional shape and support to the shroud to allow for the functioning of other features. Certain portions of the perimeter stitching on the panels are absent which allows for strap 16 to travel underneath the panels as shown. Strap 16 travels through a lower edge of each side panel 92a,b between the shroud and each panel at 107a,b, and travels up through center panel 91 to a grommet 103 formed at its center. A preferred thickness for belt/strap 16 is 2 inches. A seamless portion 85 of the belt 16 is threaded through grommet 103 and through a slot 102 formed in windlass rod 93. A retention means 94, such a short belt having quick-connectors at each end, is positioned adjacent to rod 93 and affixed to the top surface of panel 91 with stitching. Such a configuration allows for bilateral rotation 99 of rod 93 along axis 101 to tighten belt 16 around patient 12. Retention means 94 is connected around an end of rod 93 to prevent loosening of strap 16 once tightened. As may be understood, retention means 94 may include any number of securing strategies, such as for example material loops, ties, a short strap with a snap buckle, etc.

In embodiment 90, base plate 18 is made of rigid material and is affixed to the underside of shroud 104 to resiliently support its center upper portion and the center panel 91. Satisfactory dimensions for base plate 18 are 17 cm by 16 cm. Additional shroud material depends downward from the center upper portion to surround and support bladder 20. Quick connect buckle 68 has one side affixed directly to side panel 92b by having a short portion of strap 16 stitched to side panel 92b at 111 and the other end of the strap threaded underneath the side panel and underneath central panel 91 as already described. This allows for the strap 16 to be rapidly fastened around a patient 12 at 68 and a free end of strap 16 pulled to tighten.

Central panel 91 includes another aperture in a corner at 106 through which a sheathed air supply line 60 travels. Another aperture is formed at the same location in base plate 18 and the underlying shroud material to permit supply line 60 to connect to bladder 20. The aperture allows for the supply line to connect to an air supply system 96 as shown in FIG. 12 as will be described.

The air supply system 96 includes a hand bulb pump 97, which is of typical construction for blood pressure cuffs but which is preferably of a larger 5 oz capacity. A supply line 60 connects the pump 97 to a monometer 80 having an integrated manifold and cap/clasp 108 at its end proximal to the pump 97. A second clasp 109 aligns supply line 60 along the side of the monometer proximal to the aperture 106 in the central panel 91. A screw valve 98 is positioned proximal to bulb pump 97 to allow for deflation of bladder 20 and in order to more finely control the pressure applied to the patient 12.

To ensure that bladder 20 inflates in an orientation with its "V" shaped lower edge pointing downward toward a patient 12, a shock cord is placed along the bladder apex surface and a channel formed within a shroud seam at midline to prevent bladder slippage within the shroud material during inflation. The shock cord ends have tied knots which are sewn into the seam between the side 92 and central 91 panels to secure the cord to the shroud. This allows for biasing of the lower edge of the bladder within its surrounding shroud material during inflation.

In operation of embodiment 90, the inflation shape and positioning of the bladder relative to the patient 12 are the same as previously described in the other embodiments. The tourniquet is fastened around the patient such that the bladder lower edge is positioned to target location 14 such that the bladder lower edge bisects location 14. Strap 16 is pulled tight around the patient and bulb 97 is compressed by hand to inflate bladder 20 to a desired pressure. Windlass rod 93 may then be rotated to further tighten strap 16 until the desired occlusion of the abdominal aorta occurs. Retention means 94 is then be fastened around one end of rod 93 to secure the windlass and stabilize the achieved pressure.

While I have shown my invention in one form, it will be obvious to those skilled in the art that it is not so limited but is susceptible of various changes and modifications without departing from the spirit thereof. For example, tourniquet can be repositioned to occlude axial blood vessels in the abdomen leading to the arms, or blood vessels into the neck. The device may be lowered to surround the inguinal area of the body to occlude blood vessels in that area, or further, a re-sized version of the tourniquet might be utilized on a thigh or leg portion, or an arm portion to effect homeostasis in blood vessels in those areas. In all cases, however, occlusion of a targeted blood vessel achieves cessation of hemorrhage in an injury site different from the point of blood vessel occlusion.

It will also be seen that the tourniquet may be utilized to restrict blood flow at a downstream location rather than total cessation of blood flow, or for other therapeutic purposes. For example, the device may utilized to restrict blood flow through the aorta in order to "reduce" blood flow to lower the extremities during various medical procedures, and occlusion of the aorta may be utilized in order to prevent blood from leaving the patient's core to elevate the patient's blood pressure in order to enhance CPR.

Having set forth the nature of the invention, what is claimed is:

1. A method for applying a tourniquet to the abdominal region, comprising the steps of:
    a. providing an abdominal tourniquet comprising:
        i. an adjustable waist strap for securing said abdominal tourniquet around an abdomen;
        ii. a base plate carried by said waist strap having a width greater than said waist strap so that said base plate extends laterally outward from said waist strap to provide a stable base for positioning over a selected area of said abdomen;
        iii. an air bladder carried on a bottom side of said base plate having a deflated condition wherein said air bladder is collapsed against said base plate, and an inflated condition wherein said air bladder is expanded to extend outwardly from said bottom side of said base plate;
        iv. said air bladder having a generally elongated "V" shaped construction so that a wide end of said directed air bladder is generally carried on said bottom side of said base plate and an elongated narrow converging end of said directed air bladder forms an elongated edge positioned away from and parallel to said base plate;
        v. an air source operatively connected in fluid communication with said directed air bladder for operating said directed air bladder between said deflated condition and said inflated condition;
        vi. a windlass rod attached to said waist strap wherein rotation of said windlass rod tightens said waist strap; and
        vii. retention means for retaining said windlass rod in position;
    b. securing said waist strap around an abdomen of a person, wherein said air bladder is in contact with the surface of said abdomen and positioned over the aorta at or above the umbilical region of said person;
    c. inflating said air bladder with said air source;
    d. selectively actuating said windlass rod to tighten said waist strap; and,
    e. wherein said inflation step causes said elongated edge of said directed air bladder to apply a constricting force against said abdomen such that said aorta is compressed to occlusion.

2. The method of claim 1, wherein said abdominal tourniquet includes a compression latch carried on said base plate operatively associated with said waist strap for tightening said waist strap around said abdomen.

3. The method of claim 2, wherein said compression latch includes a latch base mounted to a top side of said base plate in a fixed arrangement with a first distal end of said waist strap;
    a. a latch arm pivotally mounted to said latch base operable between a closed position adjacent said latch base and an open position extending upward from said latch base; and,
    b. a terminal pivot arm pivotally carried by said latch arm having a second distal end of said waist strap secured thereto, wherein said terminal pivot arm is moved from a relaxed position to a tightened position when said latch arm is operated from said open position to said closed position so that said waist strap is shortened to tighten around said abdomen.

4. The method of claim 1, wherein said abdominal tourniquet includes a foam pad carried on said bottom side of said base plate disposed between said air bladder and said base plate to cushion said base plate against said abdomen when said air bladder is in said deflated condition.

5. The method of claim 1, wherein said abdominal tourniquet includes a protective bladder sleeve surrounding said air bladder in both said inflated and collapsed conditions to resist puncture and protect against environmental exposure of said air bladder.

6. The method of claim 1, wherein said abdominal tourniquet includes an inflation control valve carried by said air bladder in fluid communication with said air source and an interior cavity of said air bladder for controlling the flow of air into and out of said air bladder.

7. The method of claim 6 wherein said inflation control valve extends though said base plate for cooperating with said air source on a top side of said base plate.

8. The method of claim 1, wherein said air source comprises a compressed gas cartridge and said abdominal tourniquet further includes a pressure relief valve operatively connected to said gas cartridge, and wherein said abdominal tourniquet includes an elbow connecting valve disposed between said inflation control valve and said compressed gas cartridge so that said compressed gas cartridge extends generally parallel to said base plate when engaged with said elbow connecting valve.

9. The method of claim 1, wherein said abdominal tourniquet further includes at least one guide marker carried on said base plate, said guide marker configured to direct a user of said abdominal tourniquet to position said base plate in an optimal location for pressing against said abdominal aorta upon inflation of said air bladder by aligning said marker along the midline of said person.

10. A method for using an abdominal aortic tourniquet to stop bleeding in a person comprising:
    a. providing an abdominal aortic tourniquet, comprising:
        i. an adjustable waist strap for securing said abdominal aortic tourniquet around an abdomen of a person;
        ii. tensioning means connected to said waist strap wherein actuation of said tensioning means tightens said waist strap;
        iii. a directed air bladder mounted to said waist strap having a generally cuneiform shaped construction having a narrow converging end extending away from said adjustable waist strap to form an edge parallel to said strap, said air bladder operable between a deflated condition wherein said directed air bladder is collapsed, and an inflated condition wherein said directed air bladder is expanded for exerting pressure by said edge into said abdomen; and,
        iv. an air source connected to said directed air bladder for operating said directed air bladder between said deflated condition and said inflated condition;
    b. securing said waist strap around an abdomen of said person, wherein said directed air bladder is in contact with the surface of said abdomen and positioned over the abdominal aorta of said person above the inguinal area of said person;

c. inflating said directed air bladder with said air source;

d. actuating said tensioning means to tighten said waist strap; and e. wherein said inflation step causes said edge to apply a deforming force across and against said aorta to occlude said same, and wherein said inflation step causes cessation of said bleeding at a location below and away from said point of aortic occlusion.

11. In a human experiencing a hemorrhage below the inguinal area of the body, an abdominal tourniquet adapted for achieving hemostasis at said hemorrhage site comprising:

a. an adjustable waist strap adapted for securing said abdominal tourniquet around an abdomen of said body, said tourniquet including a windlass mechanism operatively connected to said waist strap for tightening said strap;

b. a base plate carried by said waist strap and configured to provide a stable base therefrom, and wherein said base plate is adapted to be positioned over the abdominal aorta above the inguinal area of said body;

c. an air bladder carried on a bottom side of said base plate having a deflated condition wherein said air bladder is collapsed against said base plate, and an inflated condition wherein said air bladder is expanded to extend outwardly from said bottom side of said base plate toward said aorta; and, d. said air bladder having an elongated "V" shape and configured so that when in said inflated condition a tip of said bladder penetrates said abdomen and occludes said aorta, and wherein said occlusion results in hemostasis at said hemorrhage site below the inguinal area of the body, and wherein the tip of said air bladder comprises an elongated edge traversing the length of said bladder and generally equidistant from said base, wherein said elongated edge of the bladder is structured and dimensioned such that when said bladder is positioned over said aorta, said edge traverses said aorta to ensure occlusion of said aorta when said bladder is secured over the abdomen of said body and inflated; and, e. an air source operatively connected to said air bladder for inflation of said same.

12. An abdominal tourniquet as recited in claim 11, further including a guide marker positioned on said base plate, said guide marker configured to direct a user of said tourniquet to position said tourniquet in an optimal occlusion location with respect to said aorta by aligning said marker along the midline of said body.

13. An abdominal tourniquet as recited in claim 12, wherein said air source comprises a compressed gas cartridge, and wherein said tourniquet includes an inflation control valve and a pressure relief valve.

14. An abdominal tourniquet as recited in claim 13, wherein said tourniquet is positioned such that said aortic occlusion results in hemostasis at a location different than said aorta occlusion location.

15. An abdominal tourniquet as recited in claim 11, wherein said tourniquet is positioned on said body such that said bladder occludes said aorta at a blood flow position upstream of and removed from said hemorrhage site.

16. An abdominal tourniquet, comprising:

a. an adjustable waist strap for securing said abdominal tourniquet around an abdomen;

b. a base plate carried by said waist strap and configured to provide a stable base therefrom, and wherein said base plate is positioned over the abdominal aorta above the inguinal area of the body;

c. an air bladder carried on a bottom side of said base plate having a deflated condition wherein said air bladder is collapsed against said base plate, and an inflated condition wherein said air bladder is expanded to extend outwardly from said bottom side of said base plate;

d. said air bladder having an elongated "V" shape and configured so that when in said inflated condition a tip of said bladder penetrates said abdomen and occludes said aorta; wherein the tip of said air bladder comprises an elongated edge traversing the length of said bladder and generally equidistant from said based, wherein said elongated edge of the bladder is structured and dimensioned such that when said bladder is positioned over said aorta, said edge traverses said aorta to ensure occlusion of said aorta when said bladder is secured over the abdomen of said body and inflated;

e. tensioning means mechanically connected to said strap for tightening said strap; and, f. an air source operatively connected to and in fluid communication with said air bladder for operating said air bladder between said deflated condition and said inflated condition.

17. An abdominal tourniquet as recited in claim 16, wherein said tourniquet is positioned such that said tourniquet applies a minimum of 120 pounds per square inch effective force across said aorta when said bladder is in said expanded condition.

18. An abdominal tourniquet as recited in claim 17, wherein said air source comprises a compress gas cartridge, and wherein said tourniquet includes an inflation control valve and a pressure relief valve.

19. An abdominal tourniquet as recited in claim 16, wherein said bladder is positioned solely at or above the umbilical region of said body.

20. An abdominal tourniquet as recited in claim 16, wherein said tourniquet is positioned such that said aorta occlusion results in hemostasis at a location different than said aorta occlusion location.

21. In a human experiencing bleeding at or below the inguinal area of the body, a method for achieving homeostasis at said site of bleeding comprising the steps of:

a. providing a tourniquet comprising:

i. an adjustable waist strap adapted for securing said tourniquet around an abdomen of said body;

ii. a base plate carried by said waist strap and configured to provide a stable base therefrom;

iii. an air bladder carried on a bottom side of said base plate having a deflated condition wherein said air bladder is collapsed against said base plate, and an inflated condition wherein said air bladder is expanded outwardly from said bottom side of said base plate;

iv. said air bladder having an elongated "V" shape and configured for resilient expansion downward;

v. a windlass rod mechanically connected to said waist strap wherein rotation of said windlass rod tightens said waist strap; and, vi. an air source operatively connected to and in fluid communication with said air bladder for operating said air bladder between said deflated condition and said inflated condition;

b. securing said waist strap around an abdomen of a person and tightening said strap with said windlass rod, wherein said air bladder is in contact with the surface of said abdomen and positioned over said aorta at or above the umbilicus region of said person;

c. inflating said air bladder with said air source;

d. wherein said inflation step forces the tip of said air bladder into the abdomen with sufficient force to restrict blood flow in said aorta; and, e. wherein said inflation step causes blood flow control at a site below the inguinal area of the body.

22. The tourniquet method of claim 21, wherein said tip of said air bladder comprises an elongated edge traversing the length of said bladder and generally equidistant from said base, and wherein said inflation step causes said edge to traverse said aorta to ensure occlusion of said same when said tourniquet is secured over the abdomen of said body and inflated.

23. The tourniquet method of claim 21, wherein said inflation step causes aortic occlusion upstream from said site of bleeding.

24. The tourniquet method of claim 21, wherein said inflation step causes aorta occlusion at or above the abdominal aortic bifurcation in said abdomen.

25. A tourniquet, comprising:

a. an adjustable strap adapted for securing said tourniquet around a portion of a patient;

b. a base plate carried by said waist strap and configured to provide a stable base therefrom;

c. an air bladder carried on a bottom side of said base plate having a deflated condition wherein said air bladder is collapsed against said base plate, and an inflated condition wherein said air bladder is expanded outwardly from said bottom side of said base plate, said air bladder having an elongated "V" shape and configured for resilient expansion downward;

d. a material shroud surrounding said base plate and said air bladder, said shroud affixed to and supporting a resilient top panel and a pair of resilient side panels depending downward therefrom, said shroud and said side and top panels configured such that said strap is positioned between said shroud and said panels for free movement therebetween;

e. a windlass supported by said top panel, said windlass including a turning rod having a slot;

f. said top panel defining an aperture, wherein said strap is threaded through said aperture and said slot in said windlass rod such that rotation of said rod tightens said waist strap; and, g. an air source operatively connected to and in fluid communication with said air bladder for operating said air bladder between said deflated condition and said inflated condition.

* * * * *